United States Patent
Hospodor et al.

(10) Patent No.: US 10,849,949 B2
(45) Date of Patent: Dec. 1, 2020

(54) ESSENTIAL ELEMENT MANAGEMENT

(71) Applicant: Robert J Rapp, San Jose, CA (US)

(72) Inventors: Andrew D Hospodor, Santa Cruz, CA (US); Robert J Rapp, San Jose, CA (US)

(*) Notice: Subject to any disclaimer, the term of this patent is extended or adjusted under 35 U.S.C. 154(b) by 93 days.

(21) Appl. No.: 15/997,633

(22) Filed: Jun. 4, 2018

(65) Prior Publication Data

US 2019/0030100 A1    Jan. 31, 2019

Related U.S. Application Data (63) Continuation of application No. 14/880,260, filed on Oct. 11, 2015, now Pat. No. 9,987,319, which is a continuation of application No. 13/655,410, filed on Oct. 18, 2012, now Pat. No. 9,155,767.

(51) Int. Cl.
*A61K 36/00* (2006.01)
*A61K 36/185* (2006.01)
*B01D 11/02* (2006.01)

(52) U.S. Cl.
CPC .......... *A61K 36/185* (2013.01); *B01D 11/028* (2013.01); *B01D 11/0219* (2013.01); *B01D 11/0292* (2013.01); *A61K 2236/39* (2013.01)

(58) Field of Classification Search
CPC .................................................. A61K 36/00
See application file for complete search history.

(56) References Cited

U.S. PATENT DOCUMENTS

| | | | |
|---|---|---|---|
| 3,941,679 A | 3/1976 | Smith | |
| 4,836,302 A | 6/1989 | Heilhecker | |
| 5,024,820 A * | 6/1991 | Coutiere | B01D 11/0223 208/311 |
| 5,466,454 A | 11/1995 | Chang | |
| 6,111,119 A | 8/2000 | Trout | |
| 7,700,368 B2 | 4/2010 | Flockhart | |
| 2005/0005772 A1 | 1/2005 | Spani | |
| 2012/0095087 A1 * | 4/2012 | Hyatt | A61K 31/05 514/454 |
| 2015/0126754 A1 | 5/2015 | Fernandez Cid | |

FOREIGN PATENT DOCUMENTS

EP    995472 A1 *    4/2000

* cited by examiner

*Primary Examiner* — Qiuwen Mi
(74) *Attorney, Agent, or Firm* — Robert J Rapp (57) ABSTRACT

The invention extends the utility of apparatus used to extract medicinal cannabis compounds into an eluate by separating a portion of medicinal cannabis compounds contained within a portion of eluate at a first extraction target level providing enough clean solvent to continue extraction operations. A high efficiency concentrator such as a rotary evaporator or a wiped film evaporator processes eluate from one or more tanks or extraction vessels creating clean solvent when extraction targets are met or when clean solvent is exhausted. This manages eluate concentration levels and limits the quantity of concentrated medicinal cannabis compounds on site at any moment in time. The invention enables a business model for keeping medicinal cannabis compounds within a legal system, and reduces pollution because law enforcement would no longer have to burn large quantities of cannabis plant matter.

22 Claims, 4 Drawing Sheets

Figure 1: Mobile Extractor in Semi Cross Section

Figure 2: A Mobile Extractor Mounted on a Truck

Figure 3: Hopper Configured for Dumping

Figure 4:

ESSENTIAL ELEMENT MANAGEMENT

CROSS REFERENCE TO RELATED APPLICATIONS

The present application is a continuation of and claims priority benefits of U.S. patent application publication Ser. No. 14/880,260, filed Oct., 11 2015, now U.S. Pat. No. 9,987,319, which is a continuation of and claims priority benefit of U.S. patent application publication Ser. No. 13/655,410, filed Oct. 18, 2012, now U.S. Pat. No. 9,155,767, the disclosures of which are incorporated herein by reference.

JOINT RESEARCH AGREEMENT

At the time of the presently disclosed invention inventors Andrew D. Hospodor and Robert J. Rapp were parties to a joint research agreement.

BACKGROUND OF THE INVENTION

The federal government of the United States as typified by the Drug Enforcement Agency (DEA), Federal Bureau of Investigation (FBI), and Federal Drug Administration (FDA) consider cannabis an illegal substance with no medicinal value. In 2009 the DEA confiscated and burned 2980 metric tons (nearly 6.6 million pounds, or 7,000,000 cannabis plants) of cannabis plants nearly doubling the 1539 metric tons confiscated and burned in 2008. The FY 2012 DEA Performance Budget Congressional Submission indicates that the DEA eradicated 9,000,000 cannabis plants in FY 2010 and 2011, and projects 9,500,000 plants (over 4000 metric tons, or 8.8 million pounds) to be eradicated in FY 2013. The burning of millions of cannabis plants emits large amounts carbon, dioxin, gasoline vapors, and other pollutants into the environment.

In contrast, the medicinal use of cannabis has been legalized and regulated in the District of Columbia, and in 17 states. The legalization of medicinal cannabis in these municipalities has led to an expansion of a state regulated distribution of cannabis flowers, edible medications, and topical medications available to individuals with proper credentials or recommendations. In an effort to lead the way in providing controlled dosage medications certain technologies have been developed that include the extraction of medicinal cannabis compounds from raw cannabis in large volumes followed by incorporation of controlled dosages of medicinal cannabis compounds into edible or topical medications. For example, it is now possible to manufacture predominantly non-psychoactive medications derived from cannabis. Characteristically different forms of medical cannabis compounds can now be studied in ways not possible before.

The most significant driver for growing demand for legalized medicinal cannabis are the increasing bodies of research showing tangible benefits to individuals suffering from a plurality of ailments when using medicinal cannabis. Furthermore, no toxic or overdose effects from the use of cannabis have been medically documented.

In past years various mechanisms for extracting essential elements from raw cannabis plant material have been researched by professional scientists, until recently the extraction of medicinal compounds from cannabis has been limited to small scale extractions by authorized scientists in the academic realm or has been performed clandestinely by individuals operating outside the law. The Applicant's related patent application Ser. No. 13/066,585, now U.S. Pat. No. 8,343,553, and Ser. No. 13/506,010 relate to extracting medicinal cannabis compounds in large volumes from cannabis plant material. The invention described in this patent application extends the utility of apparatus built consistent with the Applicant's previous extraction apparatuses.

As of 2012 states with laws regulating the medicinal use of cannabis have not implemented or officially sanctioned any strategy designed to manage cannabis waste materials (cannabis leaves, trim, imperfect bud material, insect infested, or moldy plants). Cannabis plants grown by authorized medical marijuana growers produce materials have been dispensed to patients through dispensaries, yet many patients and dispensaries are not interested is cannabis leaves, cannabis trimmings, or imperfect bud material. Furthermore, moldy cannabis plant material or insect infested plant material can cause allergic reactions, fungal infections, or have other negative side effects if consumed by people with compromised immune systems. Without effective strategies for capturing medicinal cannabis compounds contained within such "waste" cannabis plant material poses a risk that these materials may be diverted into gray or black markets or end up in rivers, streams, or in landfills.

The focus of the present invention relates to an improved apparatus, process, and business methods for extracting medicinal elements from cannabis plant material and then keeping cannabinoids within a legal system without emitting vast amounts of pollution into the environment.

SUMMARY OF THE PRESENTLY CLAIMED INVENTION

The Applicant hereby incorporates by reference his earlier patent application Ser. No. 13/066,585 entitled Essential Element Extractor and Ser. No. 13/506,010 Recycling Cannabinoid Extractor into this patent application.

The Applicant's earlier inventions described in patent application Ser. No. 13/066,585 (Essential Element Extractor) and Ser. No. 13/506,010 (Recycling cannabinoid extractor) describe processes and apparatus used to extract medicinal cannabis compounds from cannabis plant material and store them in an eluate. Such an eluate contains low concentrations of medicinal cannabis compounds per unit volume of solvent is stored in a storage tank or a "dirty tank"; the Applicant's tank or entire extraction apparatus is also typically configured to be transported on or by a vehicle. After a plurality of extractions the Applicant's eluate accumulates medicinal cannabis compounds creating "dirty" solvent. Eventually clean solvent transported into the field thus becomes dirty. Sufficiently dirty solvent reduces the efficiency of the apparatus because without clean solvent to rinse the cannabis plant material after extraction a low density residue of medicinal cannabis compounds may be left on the cannabis plant matter after extraction. Furthermore, repeated extractions using dirty solvent may cause the Applicant's eluate to exceed targeted concentrations of medicinal cannabis compounds per unit volume of solvent.

The Applicant's improved invention separates a portion of medical cannabis compounds contained in a portion of an eluate creating a more concentrated portion of dirty eluate or a concentrate of medicinal cannabis compounds and a portion of clean solvent. To accomplish this, a high efficiency concentrator such as a rotary evaporator (roto-vap) or a wiped film evaporator processes eluate from the Applicant's dirty tank or eluate output from his extraction vessel or "hopper" as referred to in the Applicant's earlier patent applications referenced above and incorporated within this disclosure. The invention also includes a business model for managing essential elements contained within cannabis by keeping them within a legal system until they are consumed or destroyed. The invention is, thus, an improved apparatus, process, and a business method.

The Applicant's invention enables law enforcement to stop burning cannabis plants in the field while allowing operations in the field to continue virtually indefinitely. This eliminates the need for law enforcement to pollute the atmosphere by burning millions of pounds of cannabis they confiscate each year.

The invention also allows municipalities with medicinal marijuana laws to enact strategies for recovering medicinal cannabis compounds from waste cannabis materials and keep them within that states legal system.

The Applicant's invention thus eliminates dis-advantages inherent in diametrically opposed theaters of the debate about how cannabis should be treated in our society. It provides benefits to those who wish to regulate cannabis as a medication and to those who wish to eradicate cannabis because it is an illegal substance under Federal law.

DETAILED DESCRIPTION OF THE INVENTION

The Applicant hereby incorporates by reference his earlier patent application Ser. No. 13/066,585 entitled Essential Element Extractor and Ser. No. 13/506,010 Recycling Cannabinoid Extractor into this patent application.

The Applicant's earlier inventions described in patent application Ser. No. 13/066,585 (Essential Element Extractor) and Ser. No. 13/506,010 (Recycling cannabinoid extractor) describe processes and apparatus used to extract medicinal cannabis compounds from cannabis plant material and store them in an eluate. Such an eluate contains low concentrations of medicinal cannabis compounds per unit volume of solvent is stored in a storage tank or a "dirty tank"; the Applicant's "dirty" tank or entire extraction apparatus is also typically configured to be transported on or by a vehicle. After a plurality of extractions the Applicant's eluate accumulates medicinal cannabis compounds creating "dirty" solvent. Eventually all clean solvent transported into the field thus becomes dirty. Sufficiently dirty solvent reduces the efficiency of the apparatus because without clean solvent to rinse the cannabis plant material after extraction a low density residue of medicinal cannabis compounds may be left on the cannabis plant matter after extraction. Furthermore, repeated extractions using dirty solvent may cause the Applicant's eluate to exceed targeted concentrations of medicinal cannabis compounds per unit volume of solvent.

The Applicant's earlier inventions include an extraction vessel (a "hopper") in controlled fluid communication with one or more solvent tanks; some embodiments include a clean configured to contain clean solvent and a dirty tank configured to contain an eluate of medicinal cannabis compounds and solvent.

The Applicant's improved invention separates a portion of medical cannabis compounds contained in a portion of an eluate creating a more concentrated portion of dirty eluate or a concentrate of medicinal cannabis compounds and a portion of clean solvent. To accomplish this, a high efficiency concentrator such as a rotary evaporator (roto-vap) or a wiped film evaporator processes eluate from the Applicant's dirty tank or eluate output from his extraction vessel or "hopper" as referred to in the Applicant's earlier patent applications referenced above and incorporated within this disclosure. The invention also includes a business model for managing essential elements contained within cannabis by keeping them within a legal system until they are consumed or destroyed. The invention is thus an improved apparatus, process, and a business method.

The Applicant's current invention extends the utility and efficiency of the Applicant's earlier inventions because clean solvent may be produced to continue field operations. Without the ability to create at least a small amount of clean solvent, field operation would have to be paused until additional clean solvent were transported on site.

A high efficiency concentration apparatus is an apparatus capable of quickly concentrating at least a portion of medicinal cannabis compounds by separating them from solvent used in previous extractions. Examples of a high efficiency concentration apparatus include a wiped film evaporator or a rotary evaporator (roto-vap), each are evaporative separators. Here again the Applicant's apparatus or portion of the Applicant's apparatus are typically configured for transport one or by a vehicle.

After the Applicant's extraction apparatus completes a plurality of extractions, the Applicant's dirty tank will contain a "targeted volume of eluate" or an eluate that contains a "targeted concentration level of medicinal cannabis compounds per unit volume of solvent".

The Applicant hereby defines the term "extraction targets" to mean either a "targeted volume of eluate" or a "targeted concentration level of medicinal cannabinoids per unit volume of solvent".

The Applicant also hereby defines "extraction target tiers" as meaning either a set of increasing "targeted volumes of solvent" or a set of increasing "targeted concentration levels of medicinal cannabis compounds per unit volume of solvent".

In some embodiments of the Applicant's invention, the total amount of medicinal cannabis compounds or the density of medicinal cannabis compounds contained in one eluate or in a plurality of eluates can be controlled by using pre-determined regimens.

The Applicant's improved invention couples a high efficiency concentration apparatus to his dirty tank and/or to his hopper for use when required or desired. For example, the high efficiency concentration apparatus may be used to separate a portion of the medicinal cannabis compounds from a portion of dirty solvent. The high efficiency concentration apparatus would have two outputs: 1. a more concentrated eluate or a concentrate of medicinal cannabis compounds; 2. clean solvent.

Extraction targets may be set based on various parameters that include yet are not limited to: volumes of eluate, measurements of eluate concentration, or combination thereof. Extraction targets include yet are not limited to: the weight of cannabis plant matter extracted within a volume of solvent, the number of plants or portion of plants extracted within a volume of solvent, a measurement of the volumetric density of medicinal cannabis compounds contained within the Applicant's eluate, a visual indication such as the opaqueness of the Applicant's eluate, and/or measurement of residual medicinal cannabis compounds contained within cannabis plant matter after extraction.

The Applicant's invention also controls eluate concentration density in various ways and may be configured to concentrate desired amounts of eluate to produce a desired amount of clean solvent. The Applicant's improved invention allows more raw cannabis to be extracted into eluate on an as needed basis. When certain extraction targets are met and more cannabis becomes available, controlled amounts of clean solvent may be produced allowing field operations to continue.

- For example, if a first target concentration density of medicinal cannabis compounds is 0.5 milligrams per milliliter of solvent was attained, a concentration protocol could be initiated wherein 25 liters of eluate were separated into 20 liters of clean solvent and 5 liters of more concentrated eluate. The concentration density of medicinal cannabis compounds in the more concentrated second eluate would be 2.5 milligrams per milliliter (12.5 milligrams in 5 liters).
- The more concentrated eluate then could be a. Mixed back into the dirty tank slightly increasing the concentration density in the dirty tank, b. Stored in a second dirty tank, or c. Concentrated further and cared for under a security protocol.
- This process could be repeated until a. A second target concentration density of medicinal cannabis compounds is reached in the dirty tank, b. The second dirty tank is full, or c. The concentrate is moved offsite or destroyed as required by a desired security protocol.

The Applicant's invention is not limited any specific targeted concentration of eluate as virtually any target concentration of medicinal cannabis compounds per unit volume of solvent may be set.

The Applicant's process and apparatus scales from smaller (pickup/flatbed truck sized), to medium (semi-truck sized), and to fixed placed stationary factory embodiments

- Another example of the Applicant's invention includes a wiped film evaporator connected to a dirty tank or to an extraction vessel such as the Applicant's "hopper". When an extraction target is met or exceeded a certain amount of eluate can be transferred from the Applicant's dirty tank and/or the Applicant's hopper to the wiped film evaporator.
- Such a wiped film evaporator configured to separate 75% of solvent from 100 liters of eluate in a single pass would provide 75 liters of clean solvent and 25 liters of a more concentrated eluate. If the initial eluate contained 10 milligrams of medicinal cannabis compounds per milliliter of eluate, 100 liters of such an eluate would contain 100 grams of medicinal cannabis compounds. The more concentrated eluate would contain 100 grams of medicinal cannabis compounds in 25 liters of eluate or 40 milligrams of medicinal cannabis compounds per milliliter of eluate after one pass through the wiped film evaporator. If the eluate were cycled through the wiped film evaporator many times additional clean solvent and a concentrate of medicinal cannabis compounds would be created.
- The Applicant's notes that his improved invention also prevents the accumulation of a residue of medicinal cannabis compounds on extracted plant matter, because clean solvent would always be available to rinse the cannabis plant matter after an extraction.

In certain embodiments the Applicant's improved invention creates a concentrate of medicinal cannabis compounds; the presence of such a concentrate is at higher risk of being stolen than the Applicant's eluate because it is a highly valued drug substance in a concentrated form. In order to mitigate the possibility of theft security protocols or conventions may be incorporated into the operation of the Applicant's improved invention.

- Security conventions include yet are not limited to a plan, a set of rules, or an apparatus used to protect or destroy the concentrated medicinal cannabis compounds.
- Examples of security protocols/conventions:
  - On site law enforcement or authorized personnel that take possession of concentrated medicinal cannabis compounds as they are produced.
  - The destruction of concentrated medicinal cannabis compounds on site by authorized personnel, or by law enforcement.
  - Supervision of all extraction/concentration activities by authorized personnel, or law enforcement.
  - The immediate incorporation of the concentrated cannabis compounds into medicinal products on site.
  - The secure isolation and transport of concentrated medicinal cannabis compounds to a facility where they may be incorporated into medicinal products or destroyed.
  - Transportation of extractors on separate vehicles from high efficiency concentration apparatuses.
  - The sequestering of medicinal cannabis compounds into elements that cannot be consumed, eaten, or smoked.
  - The vaporization of medicinal cannabis compounds from a concentrate of medicinal cannabis compounds.
  - Obfuscation of the presence of high efficiency concentration apparatuses on a vehicle transporting extraction apparatuses.

Preferred embodiments of the invention are configured to transport the Applicant's eluate containing a low concentration of medicinal cannabis compounds per unit volume of solvent without transporting a concentrate of medicinal cannabis compounds on or by the same vehicle as the Applicant's eluate, extraction apparatus, or highly efficient concentration apparatus. In these embodiments a thief would not have easy access to concentrated medicinal cannabis compounds.

Embodiments of the invention where an extraction apparatus is transported on or by a vehicle and a highly efficient concentration apparatus are transported on or by a different vehicle; thieves who stole one apparatus and not the other would not be enabled to perform both extractions and concentrations because they would only have one apparatus and not the other.

The Applicant's invention enables law enforcement to stop burning cannabis plants in the field while allowing operations in the field to continue virtually indefinitely. This eliminates the need for law enforcement to pollute the atmosphere by burning millions of pounds of cannabis they confiscate each year.

The invention also allows municipalities with medicinal marijuana laws to enact strategies for recovering medicinal cannabis compounds from waste materials and keep them within that states legal system.

The Applicant's invention thus eliminates dis-advantages inherent in diametrically opposed theaters of the debate about how cannabis should be treated in our society. It provides benefits to those who wish to regulate cannabis as a medication and also to those who wish to eradicate cannabis because it is an illegal substance under Federal law.

The invention also enables a new business model that may be operated under the supervision of law enforcement eradicating cannabis while minimizing pollution, or under the authorization of state medical marijuana laws.

The business method includes:
The authorized extraction of medicinal cannabis compounds from cannabis plant matter in the field.
Security by containing low concentrations of medicinal cannabis compounds into a volume of solvent.
Secondary security measures that regulate how concentrates are to be handled in the field and/or in a secure processing facility.
Apparatus in such a business model may be operated by the principal who developed the technology on a contractual basis, may be operated by authorized leases, or by licensing the technology to entities regionally.
The apparatus of the invention is not limited to a single extraction system, hopper (extraction vessel), solvent tank, or high efficiency concentrator. The invention may contain a plurality of hoppers, extraction systems, solvent tanks, or high efficiency concentrators. Check valves may also be incorporated into the invention to prevent back flow from one vessel or portion of the apparatus and another. Nonflammable gas may also be introduced into one or more of the vessels in the apparatus and may be used to displace oxygen or be applied under pressure to facilitate fluid flow from one vessel to another. Pressure relief valves may also be used to prevent over pressurization of a tank and be used to vent excess nonflammable gas to the environment or to a solvent vapor trap. A solvent vapor trap may contain a filter such as an activated carbon filter or include a cooled tank or compensator. A preferred nonflammable gas is nitrogen.

DETAILED DESCRIPTION OF THE DRAWINGS

Figure 1:
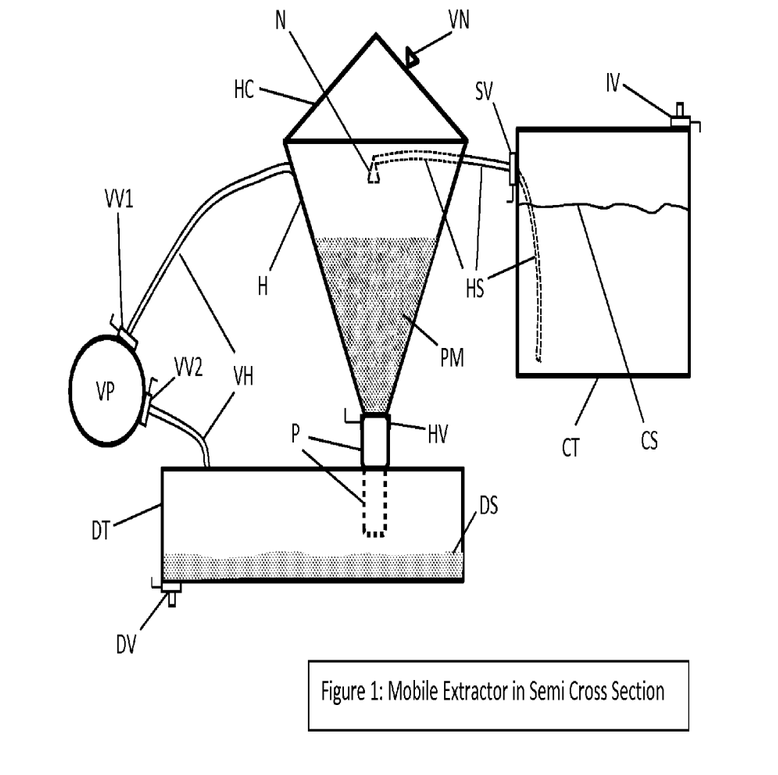
FIG. 1 illustrates an exemplary "Mobile Extractor in Semi Cross Section."

FIG. 1 illustrates an exemplary "Mobile Extractor in Semi Cross Section." FIG. 1 entitled "Mobile Extractor in Semi Cross Section" shows:
A clean tank CT filled with a clean solvent CS; a hopper H with hopper cover HC is connected to the clean tank CT by a hose HS, portions of the hose HS within the clean tank CT and within the hopper H are shown with dashed lines indicating that a portion of the hose H is inside the hopper H and inside the clean tank CT.
Inside of the hopper H is a nozzle N (shown with dashed lines) and plant material PM is shown in gray. The hopper is connected to a hopper valve HV to the dirty tank DT by a pipe P. When the hopper valve is closed solvent will not flow from the hopper H to the dirty tank DT. The dirty tank is shown containing a portion of dirty solvent DS. The hopper also is depicted as having a vent, item VN.
A solvent valve (fuel or solvent pump) item SV is located on the clean tank and is attached to hose HS, the solvent valve when open will allow clean solvent CS to be sucked into the hopper by the vacuum pump VP. When closed solvent valve SV will block the flow of clean solvent CS from the clean tank to the hopper. Item SV alternatively may be a conventional fuel pump used to pump solvent from the clean tank to the hopper. The solvent valve item SV may alternatively be a pump configured to pump solvent (i.e.: a fuel or solvent pump) that actively pumps solvent from the clean tank to the hopper.
Vacuum hoses connect the vacuum pump VP to the hopper H and to the dirty tank DT. Two separate vacuum valves VV1 and VV2 connect two separate vacuum hoses VVH to the hopper H and to the dirty tank DT respectively. Each valve VV1 and VV2 may be operated independently; they provide vacuum pressure to the mobile extractor as desired. When VV1 is open, the hopper H has a vacuum applied to it, when VV2 is open the dirty tank DT has a vacuum pressure applied to it.
By opening vacuum valve 1 VV1, when vacuum valve 2 VV2 is closed, a vacuum pressure is applied to the hopper H, this causes solvent to be sucked into the hopper from the clean tank CT when the solvent valve SV is open. At this point in time hopper valve HV is typically closed. The vacuum will cause the hopper H to fill with clean solvent CS. This is when the plant material is soaked or washed with clean solvent CS.
Evacuating the hopper: When vacuum valve 1 VV1 is open, when vacuum valve 2 VV2 is closed, when the hopper valve HV is open, and when the solvent valve SV is closed solvent will be sucked and forced by gravity into the dirty tank DT through pipe P; In this state vacuum pressure is applied to the hopper H and the dirty tank DT causing the hopper H to be sucked dry, vent, item VN if opened slightly will allow air to enter the hopper increasing the efficiency of this process. Typically a screen or filter (not depicted) located between the hopper H and the hopper valve HV will prevent plant material PM from falling into the dirty tank DT. A portion of pipe P extending into the dirty tank DT is shown with dashed lines. The Applicant's hopper valve HV may be a pump configured to pump solvent (such as a fuel or solvent pump).
Rinsing the plant material: When vacuum valve 1 VV1 is open, when solvent valve SV is open, when hopper valve HV is open clean solvent CS will be sucked from the clean tank CT into the hopper H, through the plant material PM, and into the dirty tank DT; at this point in time vacuum valve 2 will typically be closed, yet if vacuum valve 2 VV2 were open the plant material PM would still be rinsed by the solvent and the solvent would still flow into the dirty tank DT becoming dirty solvent DS. In this state vacuum pressure may be applied to the entire system.
Also connected to the clean tank is input valve IV, this valve is typically closed, yet may be opened to add more clean solvent CS into the clean tank CT.
Another valve, the drain valve DV is connected to the bottom of the dirty tank DT, the drain valve DV is typically closed, yet when open will cause the dirty solvent DS to drain out of the dirty tank DT.

Figure 2:
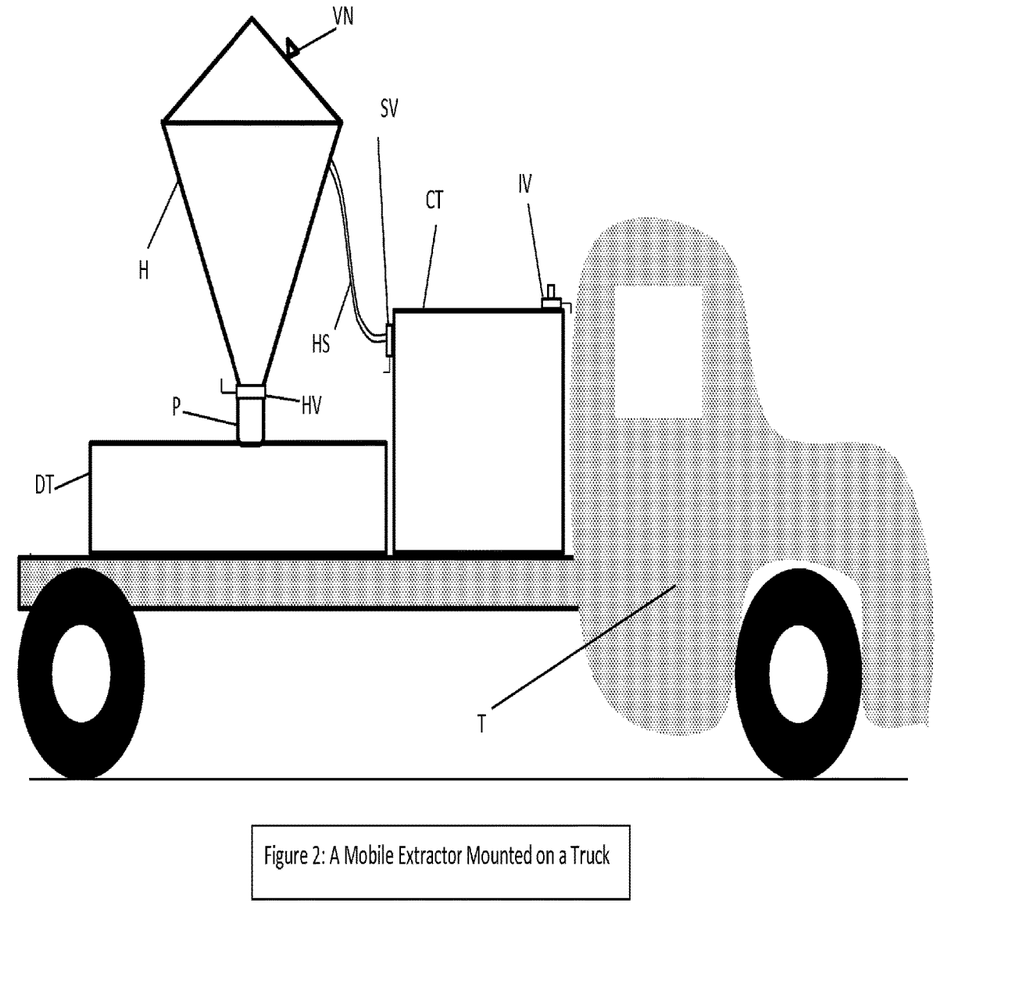
FIG. 2: illustrates an exemplary "Mobile Extractor Mounted on a Truck."

FIG. 2: illustrates an exemplary "Mobile Extractor Mounted on a Truck." FIG. 2: entitled "A Mobile Extractor Mounted on a Truck" shows:
A truck T on which elements of the mobile extractor are mounted: the clean tank CT with input valve IV and solvent valve SV are depicted.
The solvent valve SV (or pump) is again connected to the hopper H by a hose HS; the hopper H is connected to a hopper valve HV (or pump configured to pump solvent) which in turn is connected to a pipe P and to the dirty tank DT; a vent VN on the hopper is also depicted. For sake of clarity the vacuum pump, vacuum hoses, vacuum valves, and the drain valve that were depicted in FIG. 1 are not shown in FIG. 2.

Figure 3:
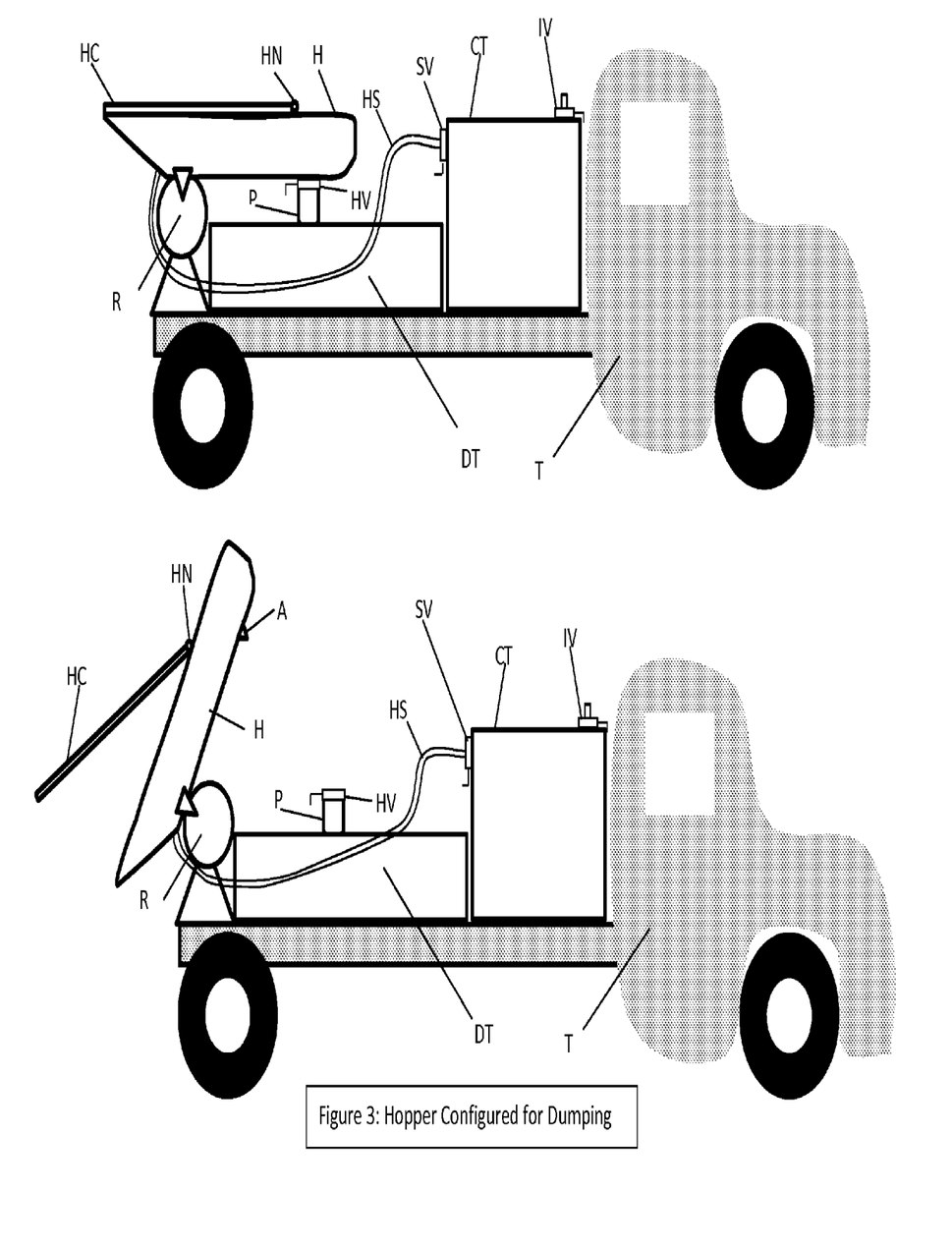
FIG. 3: illustrates an exemplary "Hopper Configured for Dumping".

FIG. 3: illustrates an exemplary "Hopper Configured for Dumping". FIG. 3: entitled "Hopper Configured for Dumping" depicts a wheel barrow shaped hopper H on truck T.

The top figure in FIG. 3 shows the hopper H in its working position. Also depicted are hopper cover HC with a hinge HN, hose HS, solvent valve or fuel pump, item SV, the clean tank CT, the dirty tank DT, a hopper valve (or pump) HV, a pipe P connecting the hopper valve HV to the dirty tank DT, and input valve IV. Item R is a rotational member; it is an apparatus that allows the hopper H to be rotated and dumped. The bottom figure in FIG. 3 shows all of the elements mentioned above (hopper H, hinge HN, hopper cover HC, hose HS, solvent valve or fuel pump SV, clean tank CT, dirty tank DT, hopper valve (or pump) HV, pipe P, input valve IV, and rotational member R) yet shows the hopper H in the dumping configuration where hopper cover HC opens using hinge HN; this allows contents of the hopper H to be dumped. Also depicted is adaptor A, adaptor A allows the hopper to be connected to hopper valve (or pump) HV in a secure way.

Note that hose HS connects to the hopper near the point of rotation R of the hopper H, this allows the hopper H to be dumped without stressing or pulling on the hose HS.

The Applicant notes that the apparatus depicted in his FIGS. 1-3 depict embodiments of apparatus consistent with his earlier invention, those inventions are not limited to these embodiments.

Figure 4:
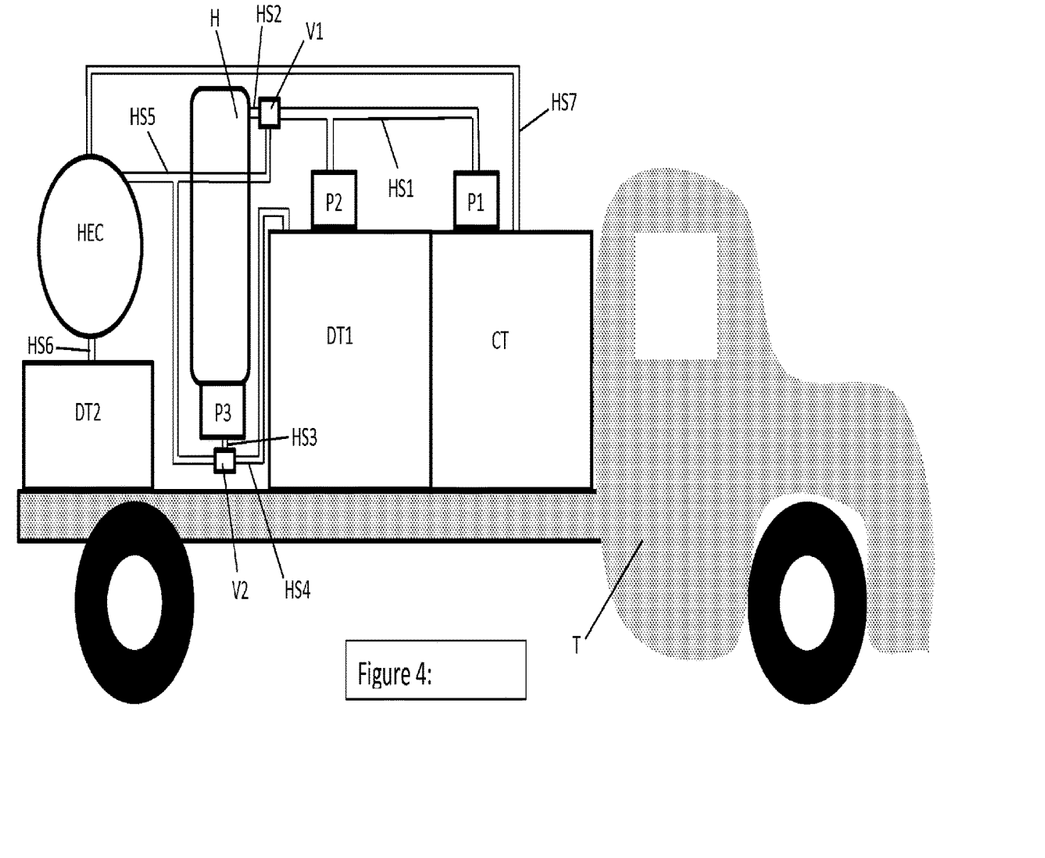
FIG. 4: illustrates an exemplary truck containing a clean tank, a first dirty tank, a hopper, pumps, valves, and a high efficiency concentrator.

FIG. 4: illustrates an exemplary truck containing a clean tank, a first dirty tank, a hopper, pumps, valves, and a high efficiency concentrator. FIG. 4: The Applicant's FIG. 4 depicts a truck T containing a clean tank CT, a first dirty tank DT1, a hopper H, pumps P1 P2 and P3, valves V1 and V2, a high efficiency concentrator HEC, a second dirty tank DT2, and hoses (or pipes) HS1 through HS7.

The extraction system includes the clean tank CT, the first dirty tank DT1, the hopper H, pumps P1 P2 and P3.

Valve V1 is configured to switch solvent flow from hose HS1 to the hopper H through valve V1 and hose HS2, or from hose HS1 to the high efficiency concentrator HEC through valve V1 and hose HS5. Valve V1 thus is configured to control whether eluate flows from the first dirty tank DT1 through pump P2 and into the hopper H or into the high efficiency concentrator when pump P2 pumps eluate.

Valve V2 is configured to control solvent flow from the hopper H through hose HS3, valve V2 and into the first dirty tank through hose HS4; or to the high efficiency concentrator HEC through hose HS3, valve V2, and hose HS5.

Hose HS6 is configured to transport an eluate from the high efficiency concentrator to the second dirty tank DT2. Hose HS7 is configured to transport clean solvent output by the high efficiency concentrator HEC to the clean tank.

In this embodiment the high efficiency concentrator HEC can thus separate clean solvent from an eluate sourced from the first dirty tank DT1 or from the hopper H and to create a more concentrated eluate that is stored in the second dirty tank DT2.

The invention claimed is:

1. A method for processing cannabinoids, the method comprising:
   moving a mobile vehicle to a location, the mobile vehicle transporting an apparatus for separating a cannabinoid from a cannabinoid containing substance, wherein the cannabinoid containing substance includes the cannabinoid and at least one other substance;
   introducing the cannabinoid containing substance into an input at the apparatus based on an operation of a pump;
   outputting a portion of the at least one other substance out of a first output at the apparatus; and
   outputting a portion of the cannabinoid out of at least a second output of the apparatus.

2. The method of claim 1, wherein the at least one other substance includes a portion of a solvent.

3. The method of claim 1, further comprising evaporating the portion of the cannabinoid.

4. The method of claim 1, further comprising evaporating the at least one other substance.

5. The method of claim 1, further comprising collecting the portion of the cannabinoid in a vessel, wherein the portion of the cannabinoid is measurable in milligrams.

6. The method of claim 1, further comprising providing the portion of the cannabinoid to a recipient authorized by law to receive cannabinoids.

7. The method of claim 1, further comprising controlling a flow of the cannabinoid containing substance introduced into the apparatus.

8. The method of claim 1, wherein the pump is a vacuum pump.

9. The method of claim 1, wherein the pump is a solvent pump.

10. The method of claim 1, further comprising passing an initial cannabinoid containing substance into a filter that filters the initial cannabinoid containing substance and outputs the cannabinoid containing substance.

11. The method of claim 1, wherein the portion of the cannabinoid is a first type of cannabinoid and the at least one other substance includes a second type of cannabinoid.

12. The method of claim 1, further comprising evaporating a first material from an initial cannabinoid containing substance before introducing the cannabinoid containing substance into the input of the apparatus, the initial cannabinoid containing substance including the portion of the cannabinoid.

13. The method of claim 12, wherein the evaporation of the first material is performed by a wiped film evaporator.

14. A method for cannabinoids, the method comprising:
   passing an initial cannabinoid containing substance into a filter that filters the initial cannabinoid containing substance and outputs a cannabinoid containing substance;
   introducing the cannabinoid containing substance into an input at an apparatus based at least in part on an operation of a pump, the cannabinoid containing substance including a cannabinoid and at least one other substance;
   evaporating a portion of the cannabinoid from the cannabinoid containing substance;
   outputting at least a portion of the at least one other substance out of a first output at the apparatus; and
   outputting the portion of the cannabinoid out a second output of the apparatus.

15. The method of claim 14, further comprising controlling a flow of at least one of the cannabinoid containing substance, the portion of the at least one other substance, or the portion of the cannabinoid based at least in part on an operation of one or more check valves.

16. The method of claim 14, further comprising further comprising transporting the apparatus to a location by a mobile vehicle.

17. A method for processing cannabinoids, the method comprising:
   introducing a first cannabinoid containing substance into a first evaporator that performs a first evaporation, wherein the first evaporator is a wiped film evaporator;
   performing a first evaporation that evaporates a volume of solvent from the first cannabinoid containing substance;
   introducing a second cannabinoid containing substance into a second evaporator based at least in part on the first evaporation being performed; and
   performing a second evaporation that evaporates at least one of additional solvent or a portion of a cannabinoid from the second cannabinoid containing substance.

18. The method of claim 17, further comprising performing a third evaporation that evaporates the portion of the cannabinoid from a third substance generated based at least in part on the second evaporation being performed.

19. The method of claim 17, further comprising introducing at least one of the first or the second cannabinoid containing substance into the first or the second evaporator based at least in part on an operation of a pump.

20. The method of claim 17, wherein the second evaporator is a wiped film evaporator.

21. The method of claim 17, further comprising controlling a flow of at least one of the first cannabinoid containing substance, a portion of at least one other substance, or the portion of the cannabinoid based at least in part on an operation of one or more check valves.

22. The method of claim 17, further comprising passing an initial cannabinoid containing substance into a filter that filters the initial cannabinoid containing substance and outputs the first cannabinoid containing substance.

* * * * *